(12) United States Patent
Walzman (10) Patent No.: US 11,000,672 B2
(45) Date of Patent: May 11, 2021

(54) AUGMENTED BYPASS CATHETER

(71) Applicant: Daniel Ezra Walzman, Bergenfield, NJ (US)

(72) Inventor: Daniel Ezra Walzman, Bergenfield, NJ (US)

( * ) Notice: Subject to any disclaimer, the term of this patent is extended or adjusted under 35 U.S.C. 154(b) by 200 days.

(21) Appl. No.: 16/024,038

(22) Filed: Jun. 29, 2018

(65) Prior Publication Data

US 2019/0217051 A1    Jul. 18, 2019

Related U.S. Application Data

(63) Continuation-in-part of application No. 15/932,911, filed on May 18, 2018, now Pat. No. 10,799,674, (Continued)

(51) Int. Cl.
| | | |
|---|---|---|
| *A61M 25/00* | (2006.01) | |
| *A61M 25/10* | (2013.01) | |
| *A61N 7/00* | (2006.01) | |
| *A61B 17/3207* | (2006.01) | |
| *A61M 5/14* | (2006.01) | |

(Continued)

(52) U.S. Cl.
CPC ....... *A61M 25/007* (2013.01); *A61B 17/3207* (2013.01); *A61M 25/10* (2013.01); *A61N 7/00* (2013.01); *A61B 17/12136* (2013.01); *A61B 2017/22079* (2013.01); *A61B 2017/22084* (2013.01); *A61M 5/14* (2013.01); *A61M 2025/0073* (2013.01);

(Continued)

(58) Field of Classification Search
CPC .. A61M 2025/0197; A61M 2025/1097; A61M 2025/1095; A61B 17/3207; A61B 2017/22079; A61B 2017/22084
See application file for complete search history.

(56) References Cited

U.S. PATENT DOCUMENTS

| | | |
|---|---|---|
| 4,183,102 A | 1/1980 | Guiset |
| 4,309,994 A | 1/1982 | Grunwald |

(Continued)

FOREIGN PATENT DOCUMENTS

WO    2005112823    12/2005

OTHER PUBLICATIONS

U.S. Appl. No. 15/258,877, filed Sep. 2016, Walzman.

*Primary Examiner* — Emily L Schmidt (57) ABSTRACT

An innovative medical device that permits rapid, minimally invasive restoration of blood flow across a vascular blockage. A method employing said device, allowing for lysis or removal of said blockage. Said removal of said blockage is facilitated by either or both mechanical and energy-emission maceration. Said device creates a temporary bypass using longitudinal structure configured for insertion into the blood vessel and adapted to deliver a side hole to a target area. The side hole defines a distal first segment and a proximal second segment with a lumen to allow blood flow therethrough to the distal end hole. In an alternate embodiment, a slide-able outer sheath can cover the side hole to permit reversal of blood flow from the distal end hole to a proximal end hole located outside a patient's body by means of an aspiration controller. Alternate embodiments include an optional anchoring balloon, a macerating stent or wires, perforations for fluid delivery, and a backflow valve.

18 Claims, 5 Drawing Sheets

Related U.S. Application Data which is a continuation-in-part of application No. 15/732,953, filed on Jan. 16, 2018, now Pat. No. 10,857,328.

(51) Int. Cl.
   *A61B 17/12* (2006.01)
   *A61B 17/22* (2006.01)

(52) U.S. Cl.
   CPC ............... *A61M 2025/0076* (2013.01); *A61M 2025/105* (2013.01); *A61M 2025/1095* (2013.01)

(56) References Cited

U.S. PATENT DOCUMENTS

| | | |
|---|---|---|
| 4,573,966 A | 3/1986 | Weiki |
| 4,661,094 A | 4/1987 | Simpson |
| 4,755,176 A | 7/1988 | Patel |
| 4,784,638 A | 11/1988 | Ghajar et al. |
| 4,795,427 A | 1/1989 | Helzel |
| 4,944,745 A | 7/1990 | Sogard et al. |
| 4,968,306 A | 11/1990 | Huss |
| 4,970,926 A | 11/1990 | Ghajar et al. |
| 5,087,247 A | 2/1992 | Horn et al. |
| 5,147,302 A | 9/1992 | Euteneuer et al. |
| 5,163,905 A | 11/1992 | Don Michael |
| 5,167,628 A | 12/1992 | Boyles |
| 5,180,387 A | 1/1993 | Ghajar et al. |
| 5,284,473 A | 2/1994 | Calabria |
| 5,344,402 A | 9/1994 | Crocker |
| 5,370,617 A | 12/1994 | Sahota |
| 5,411,479 A | 5/1995 | Bodden |
| 5,460,610 A | 10/1995 | Don Michael |
| 5,470,314 A | 11/1995 | Walinsky |
| 5,542,925 A | 8/1996 | Orth |
| 5,613,980 A | 3/1997 | Chauhan |
| 5,639,274 A | 6/1997 | Fischell et al. |
| 5,669,924 A | 9/1997 | Shaknovich |
| 5,720,735 A | 2/1998 | Dorros |
| 5,769,828 A | 6/1998 | Jonkman |
| 5,800,407 A | 9/1998 | Eldor |
| 5,830,181 A | 11/1998 | Thornton |
| 5,840,066 A | 11/1998 | Matsuda |
| 5,919,163 A | 7/1999 | Glickman |
| 5,947,985 A * | 9/1999 | Imran ............... A61B 17/32037 604/101.05 |
| 5,951,514 A | 9/1999 | Sahota |
| 5,954,687 A | 9/1999 | Baudino |
| 6,013,054 A | 1/2000 | Jiun Yan |
| 6,017,324 A | 1/2000 | Tu |
| 6,048,333 A | 4/2000 | Lennox |
| 6,071,285 A | 6/2000 | Lashinski |
| 6,086,557 A | 7/2000 | Morejohn |
| 6,129,704 A | 10/2000 | Forman et al. |
| 6,146,370 A | 11/2000 | Barbut |
| 6,193,685 B1 | 2/2001 | Goodin |
| 6,223,637 B1 | 5/2001 | Hansen |
| 6,296,655 B1 | 10/2001 | Gaudoin et al. |
| 6,364,900 B1 | 4/2002 | Heuser |
| 6,514,281 B1 | 2/2003 | Blaeser |
| 8,403,911 B2 | 3/2013 | Garrison et al. |
| 8,460,240 B2 | 6/2013 | Towler |
| 8,480,619 B2 | 7/2013 | Porter |
| 8,496,629 B2 | 7/2013 | McKinnon et al. |
| 8,747,456 B2 | 6/2014 | Baim |
| 8,951,226 B2 | 2/2015 | Hameed |
| 8,956,383 B2 | 2/2015 | Aklog |
| 9,295,818 B2 | 3/2016 | Riina |
| 9,364,634 B2 | 6/2016 | Adams et al. |
| 9,399,112 B2 | 7/2016 | Shevgoor et al. |
| 9,440,043 B2 | 9/2016 | Arora et al. |
| 9,579,494 B2 | 2/2017 | Kersten et al. |
| 9,642,673 B2 | 5/2017 | Adams et al. |
| 9,993,325 B2 | 6/2018 | Ren |
| 10,299,824 B2 | 5/2019 | Walzman |
| 10,328,246 B1 | 5/2019 | Walzman |
| 10,314,684 B2 | 6/2019 | Walzman |
| 10,576,245 B2 | 3/2020 | Walzman |
| 2002/0035361 A1 | 3/2002 | Houser |
| 2002/0052620 A1 | 5/2002 | Barbut |
| 2002/0165572 A1 | 11/2002 | Saadat |
| 2002/0188276 A1 | 12/2002 | Evans |
| 2003/0023204 A1 | 1/2003 | Vo |
| 2003/0097169 A1 | 5/2003 | Brucker |
| 2003/0198798 A1 | 10/2003 | Hehrlein |
| 2004/0006306 A1 | 1/2004 | Evans |
| 2004/0024347 A1 * | 2/2004 | Wilson ............... A61B 17/2202 604/22 |
| 2004/0059278 A1 | 3/2004 | McPherson |
| 2004/0122465 A1 | 6/2004 | McMurtry |
| 2005/0038420 A1 | 2/2005 | Huybregts |
| 2005/0171505 A1 | 8/2005 | Bertolero |
| 2006/0235459 A1 | 10/2006 | Das |
| 2007/0038170 A1 | 2/2007 | Joseph |
| 2007/0185445 A1 * | 8/2007 | Nahon ................ A61M 25/104 604/96.01 |
| 2007/0197997 A1 | 8/2007 | Dua |
| 2007/0225750 A1 | 9/2007 | Ren |
| 2007/0287967 A1 | 12/2007 | Hekmat |
| 2008/0039786 A1 * | 2/2008 | Epstein ............ A61B 17/12104 604/103.03 |
| 2008/0125746 A1 | 5/2008 | Shapland |
| 2008/0281394 A1 | 11/2008 | Jones |
| 2009/0209855 A1 | 8/2009 | Drilling |
| 2009/0209907 A1 | 8/2009 | Grata |
| 2011/0190727 A1 | 8/2011 | Edmunds |
| 2011/0245802 A1 | 10/2011 | Hayman |
| 2011/0276023 A1 | 11/2011 | Leeflang |
| 2012/0029436 A1 | 2/2012 | Yassinzadeh |
| 2012/0116352 A1 | 5/2012 | Rangi |
| 2012/0136242 A1 | 5/2012 | Qi |
| 2012/0302953 A1 * | 11/2012 | Don Michael ......... A61B 17/22 604/101.05 |
| 2012/0316632 A1 | 12/2012 | Gao |
| 2013/0158511 A1 | 6/2013 | Aggerholm |
| 2013/0190796 A1 | 7/2013 | Tilson et al. |
| 2014/0025151 A1 | 1/2014 | Gao |
| 2014/0148751 A1 | 5/2014 | Kassab et al. |
| 2015/0127034 A1 | 5/2015 | Eaton |
| 2015/0196303 A1 | 7/2015 | Seguin |
| 2016/0278783 A1 | 9/2016 | Magee |
| 2016/0324668 A1 | 11/2016 | Wallace et al. |
| 2017/0000493 A1 * | 1/2017 | Boehm, Jr. ......... A61B 17/1214 |
| 2017/0007800 A1 | 1/2017 | Chao et al. |
| 2017/0086860 A1 | 3/2017 | Lee |
| 2018/0126130 A1 | 5/2018 | Nitzan et al. |
| 2018/0161552 A1 | 6/2018 | Larson |
| 2018/0229010 A1 | 8/2018 | Walzman |

\* cited by examiner

AUGMENTED BYPASS CATHETER

CROSS-REFERENCE(S)

This is a continuation-in-part application claiming the benefit of priority to U.S. Non-Provisional application Ser. No. 15/932,911 filed May 18, 2018, and Ser. No. 15/732,953 filed Jan. 16, 2018, the entire contents of which are incorporated by reference.

BACKGROUND OF THE INVENTION

Field of the Invention

The present invention relates generally to medical device placed in a minimally invasive manner, most often percutaneous and endovascular; specifically, to a bypass catheter to ameliorate ischemic injury employing an energy generated tipped bypass catheter.

Discussion of the Prior Art

The use of devices in conjunction with medical procedures for controlling blood flow in a blood vessel is taught by the prior art. Among the most common is a balloon catheter. The balloon catheter, such as taught in the prior art, may be used to achieve isolation of a body part from its blood supply.

One of the problems associated with using balloons is that although control of the blood flow through a portion of the blood vessel is achieved, including blockage of the blood supply to a targeted site, blood flow is completely interrupted to other sites near the targeted site.

This shortcoming can be tolerated for a short duration because when one blood vessel becomes blocked, the body normally increases the blood flow through other, essentially paralleling blood vessels. However, complex medical procedures may not be achieved during said short duration resulting in injury to said other sites or requiring multiple operations at the same targeted site. Additionally, current bypass catheters are designed to be surgically implanted, which is not practical for immediate relief of progressive ischemia caused by a sudden blockage of a blood vessel, such as from a thrombus or embolus.

An additional shortcoming of prior art applications is related to the presence of clots. The prior art discloses both catheter bypass devices, lytic infusion catheters, and an ultrasound transmitter for breaking up clots. These clot remediation device each have their own shortcoming. Catheter bypass devices bypass clot but do not remove them, resulting in disabling said device in some instances. Lytic infusion catheters are ineffective at removing thrombus of the deep venous system, and when extensive, deep vein thrombosis carries a high risk of developing post-thrombotic syndrome and venous status ulcers. While ultrasound devices are safe, noninvasive, diagnostic tool with widespread applications in health care, to use it in conjunction with previously described bypass devices, it must be used in a serial manner. The ultrasound device must be inserted and removed prior to the use of a bypass device. Said insertion and removal tend to cause damage to vessels necessary to access the target treatment area.

The present invention surmounts the problem of complete blood interruption that causes ischemia, which if not rapidly reversed will result in permanent injury

SUMMARY OF THE INVENTION

The present invention provides an improved catheter, for use in the blood vessel system in the body, which invention includes a catheter device and method of use.

The present invention discloses an energy source combined with a bypass catheter disclosed in U.S. patent application Ser. No. 15/932,911, which is also capable of lytic infusions. One iteration of the energy source is an ultrasound transmitter system.

Acute intermediate-risk pulmonary emboli in normotensive patients with ventricle (particularly right ventricle) dysfunction present the clinician with a practical dilemma. With a three (3) percent mortality rate, acute intermediate-risk pulmonary emboli warrant therapy that will rapidly reduce ventricular strain and pulmonary artery pressure. While systemic lytics, with a 2 to 3 percent risk of catastrophic intracranial bleeding, has a major complication rate equal to the overall mortality of the disease. Yet standard anticoagulation often acts too slowly, achieving full efficacy in responsive patients over the course of weeks or even months. In addition, in massive pulmonary emboli immediate restoration of some degree of flow is needed to avoid nearly universal death that will result without treatment.

While the prior art teaches the during catheter-assisted thrombolysis treatment, a catheter is guided through blood vessels to the location of the blood clot. The catheter will deliver special clot dissolving medicine called thrombolytics to help dissolve the clot. The catheter such as the Ekos device additionally has an ultrasound element to be used in conjunction with the thrombolytic medications to help break up the clot. Said Ekos device lacks the bypass element to help provide immediate reperfusion. The present invention surmounts the lack of immediate reperfusion associated with the Ekos device, by providing immediately restoring the flow of blood to an organ or tissue. In the case of many pulmonary emboli, this bypass element can also immediately relieve strain on the heart created by resistance to outflow.

The bypass catheter disclosed in in Ser. No. 15/932,911 lacks an adjunctive energy source to help break up clot and help bound fibrin release to better accept lytic medications. The addition of the energy source such as an ultrasound component to the Walzman bypass catheter will facilitate breaking up the clots, requiring lower doses of lytics, over shorter times, and with better net effect.

It should also be noted that the prior art discloses ultrasound-assisted catheter-directed low-dose thrombolysis delivers the efficacy of systemic lytics by quickly reducing right ventricular afterload and improving right ventricle size and function, but with the lower risk profile comparable to anticoagulants alone. However, the treatment is slow. Typically, patients with acute intermediate-risk pulmonary embolis treated with ultrasound-assisted catheter-directed low-dose thrombolysis systemic lytics technology have had an average reduction in pulmonary artery systolic pressure of only 10 mmHg after 16 hours of the onset of therapy. While US20070083100A1 (Ser. No. 11/458,822—Sebastian Schulz-Stubner hereinafter 822) discloses an ultrasound embedded in the tip of the ventriculostomy. More particularly, 822 discloses a ventriculostomy catheter system with in situ ultrasound capability, wherein the ultrasonic element can remain in place at the working end of the catheter, independent of the removal of the stylet after the catheter has been positioned in its desired location. However, 822 discloses a diagnostic ultrasound to help guide placement of the catheter. It fails to disclose the use of ultrasound to ameliorate a targeted clot. Because 822 is not capable of removing the dislocated elements of a targeted clot, and failure to execute said removal will result in medical difficulties, 822 could not be used for clot removal even if the ultrasound element could displace clot elements.

BRIEF DESCRIPTION OF THE DRAWINGS

The invention will be better understood and objects other than those set forth above will become apparent when consideration is given to the following detailed description thereof Such description references the annexed drawings wherein.

DETAILED DESCRIPTION OF THE INVENTION

The present invention discloses the addition of an energy source such as ultrasound transition system to a Walzman bypass catheter Ser. No. 15/932,911.

The energy tipped bypass catheter is composed of the following elements: an energy transmitter, a structure to mount said transmitter to said bypass catheter and an activation element. Said ultrasound transition system or other energy source is designed to break up clot and, in some iterations, to help break up calcium, like a lithotripsy device.

In an optional embodiment said ultrasound transition system can have a diagnostic ultrasound. However, in the preferred embodiment said ultrasound transition system is designed to break clots, as opposed to acting as a therapeutic device. The diagnostic ultrasound element is optional embodiment.

The temporary balloon element, when present on the bypass catheter, is composed of a catheter with at least one distal end hole, at least one bypass window proximal to said end hole and a balloon element between said end hole and said bypass window. The present invention is capable of deploying said balloon element, before inflation, across a blockage in a vessel.

Figure 1:
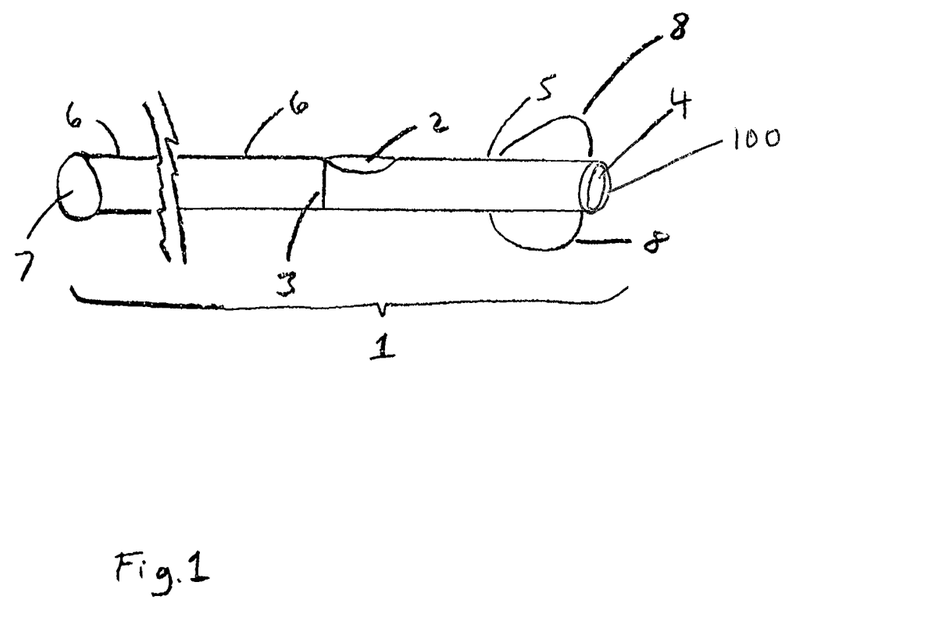
FIG. 1 is a side view of the current invention.

Referring now to FIG. 1, the current invention (1) there is a distal end hole (4) and a side hole (2) disposed upon the outer diameter of the device (1) of the current invention at the juncture of first segment (5) and second segment (6). Side hole (2) defines the end of second segment (6) through proximal end hole (7) from first segment (5) through distal end hole (4). The outer diameter of first segment (5) and second segment (6) are the same in some but not all embodiments.

The bypass catheter device (1) of the current invention is introduced through an incision in a patient's vessel and often directed to a target site by means of standard endovascular techniques, with the aid of wires and/or other delivery catheters, often under fluoroscopic guidance.

Returning to FIG. 1, first segment (5) is used to anchor device (1) so as to position side hole (2) at the desired location. Optionally, first segment (5) may be attached to a balloon (8) which, upon inflation, further anchors device (1) of the current invention in the desired position.

The present invention is positioned such that side hole (2) is positioned to accept blood flow from the patient and direct the blood through first segment (5) out through distal hole (4), bypassing said blood flow past a blockage. Proximal to and surrounding distal hole (4) is positioned energy transmitter (100). The current invention prevents backflow of blood in three ways, or any combination thereof FIG. 1 illustrates an embodiment employing valve (3) disposed at the juncture of second section (6) with side hole (2). In this embodiment, once the device (1) of the current invention is positioned in the desired position, valve (3) is closed by the user to prevent blood entering side hole (2) from flowing back into said second segment (6). The blood is thereby directed through first segment (5), through and out end hole (4), and allowed to perfuse the at-risk tissue. Proximal to and surrounding distal hole (4) is positioned energy transmitter (100). energy transmitter (100) may be powered by an ultrasound generator and the circular configuration allow energy waves to be focused in any direction and at variable force depending upon the amount of discrete energy applied to different areas of the ring which forms energy transmitter (100). In the preferred embodiment the energy transmitted by energy transmitter (100) is ultrasound.

Figure 2:
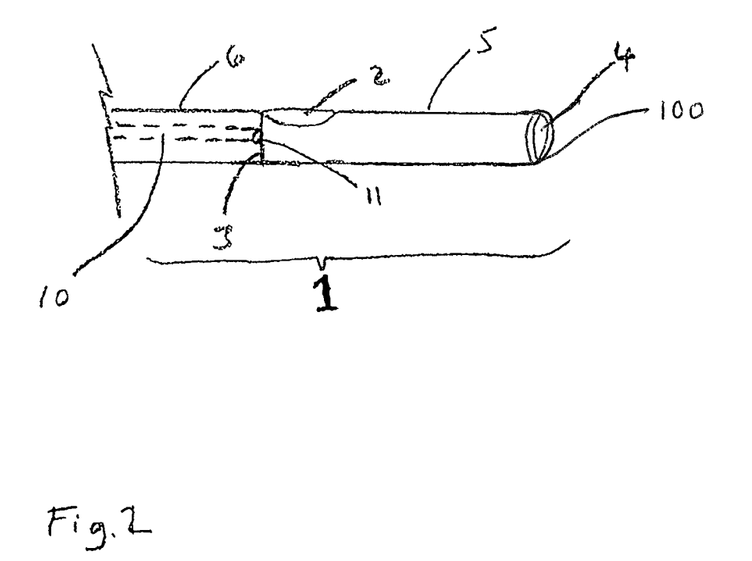
FIG. 2 is a side view of the current invention showing the inner segment with dashed lines.

In an alternative embodiment better depicted in FIG. 2, the inner diameter (10) of second segment (6) is less than the inner diameter of first segment (5). Inner diameter (10) terminates at inner hole (11). Inner hole (11) is smaller than distal end hole (4). The differential acts to constrict backflow and direct blood through first segment (5) to and out end hole (4). Proximal to and surrounding distal hole (4) is positioned energy transmitter (100).

In a preferred embodiment, a valve (3) and a reduced inner diameter (10) and inner hole (11) are employed to constrict backflow of blood.

Figure 3:
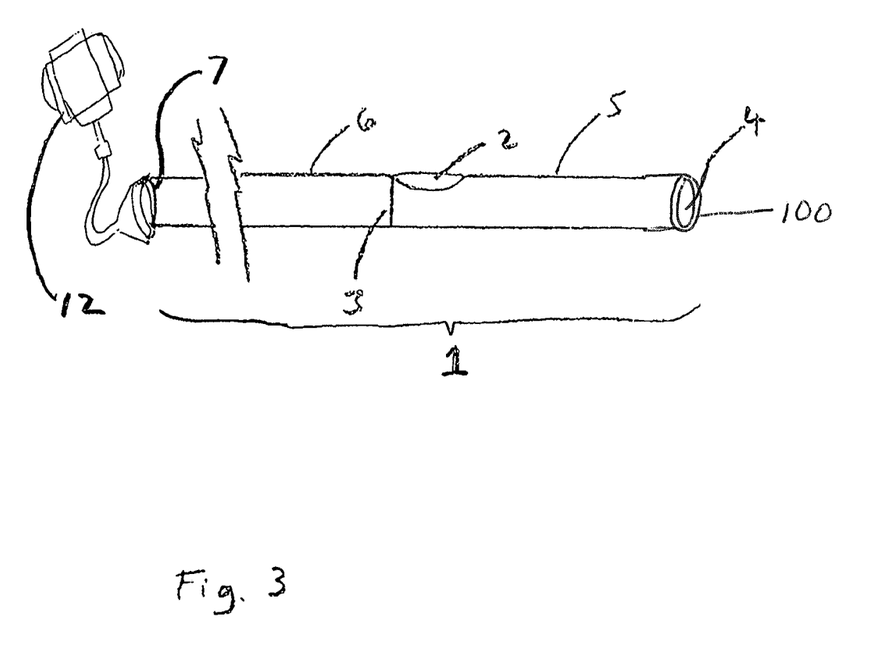
FIG. 3 depicts the first segment of the current invention connected to a pressurized fluid column.

In a still further embodiment depicted in FIG. 3, pressurized fluid may be introduced into second segment (6) to prevent the backflow of blood. FIG. 3 depicts device (1) of the current invention connected to pressurized fluid bag (12) interfacing with proximal end hole (7). Proximal end hole (7) communicates with second segment (6) through to first segment (5). Said pressurized fluid bag (12) may be connected to a flow regulator which is outside the patient's body to allow the user of the current invention to control flow of fluid through the second segment (6).

In another embodiment, pressurized fluid may be used in conjunction with valve (3) and/or inner hole (11) to prevent backflow of blood. In a still further embodiment, pressurized fluid, valve (3) and differential inner diameter (10) and inner hole (11) may be used concurrently.

Figure 4:
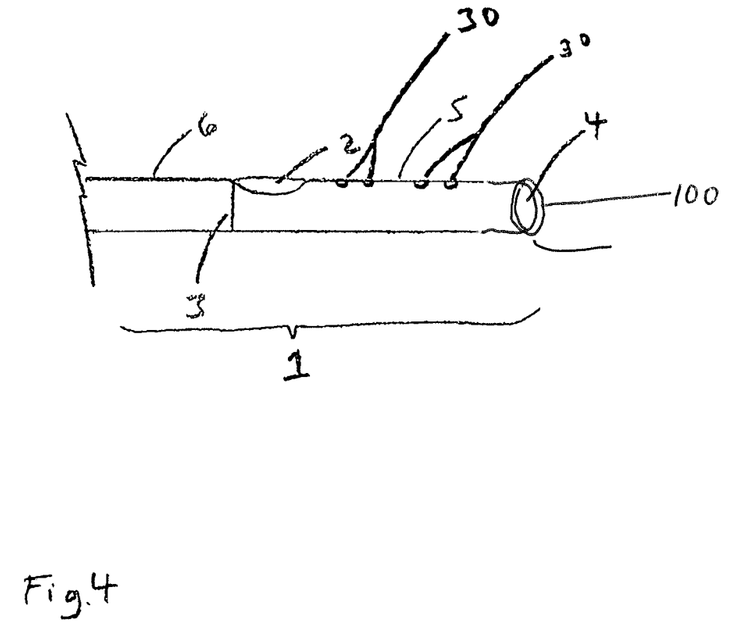
FIG. 4 is a side view of the current invention with perforations allowing infusion of medication from the proximal end.

As shown in FIG. 4, first segment (5) may optionally be perforated with at least one perforation (30). Perforations (30) are end holes for a lumen which extends from said perforations (30) and communicating with a separate irrigation channel (not shown) disposed at proximal end hole (7) and in communication with an additional controller (not shown). The fluid typically introduced into the separate channel exiting perforations (30) is designed to dissolve vessel-clogging material. For example, the fluid may be a lytic such as Alteplase, which dissolves blood clots. Said additional controller is capable of sending medication from said additional controller through communicating lumen and out perforations (30) to facilitate the irrigation of clots near first segment (5). Said medication has the capability of softening and/or changing the chemical makeup of clots proximal to perforations (30) for purposes of dislocating and/or dissolving said clot(s) or other blockage. In an alternate embodiment, the present invention device (1) is composed of co-centric lumens wherein perforations (30) communicate with the area between the internal surface of the outer lumen and the outer surface of the inner lumen, said gap extends from perforations (30) to proximal end hole (7) and communicates with said additional controller, allowing medication to be pumped from said additional controller through the area between the internal surface of the outer lumen and the outer surface of the inner lumen and out perforations (30) to allow the infusion of medication to soften, lyse, or alter the composition of clots or blockages. In the preferred embodiment, the inner channel (or area between the internal surface of the outer lumen and the outer surface of the inner lumen) terminates at the most distal perforation (30). Alternatively, the inner channel may terminate in the first segment at or near the end hole (4). Proximal to and surrounding distal hole (4) is positioned energy transmitter (100).

Figure 5:
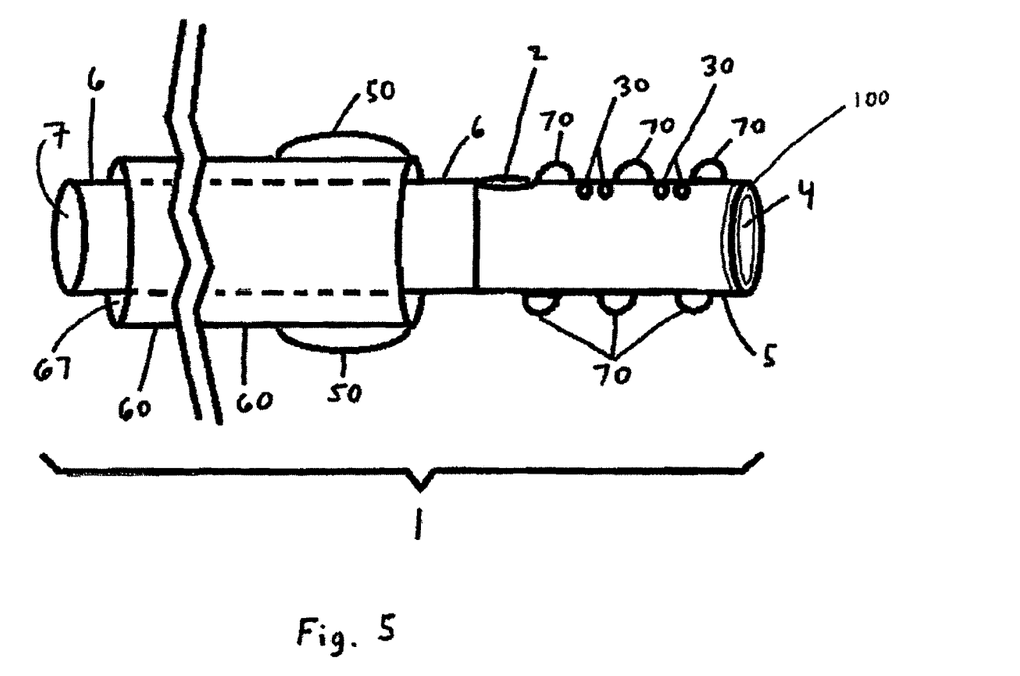
FIG. 5 depicts an alternative embodiment of the current invention.

Referring now to FIG. 5, an alternate embodiment of the device (1) of the present invention further includes rotating, macerating and irrigating elements, more particularly, a slide-able outer support sheath (60), macerating elements or loops (70), and/or perforations (30) used as irrigating elements. Said slide-able outer support sheath (60) is capable of snugly closing side hole (2) when first segment (5) is withdrawn inside of said sheath (60). This action of withdrawing side hole (2) into outer support sheath (60) results in changing the blood-flow bypass from side hole (2) through distal end hole (4), redirecting the blood flow from distal end hole (4) out proximal end hole (7) due to an aspiration controller communicating with proximal end hole (7). Also shown in this embodiment are optional backflow valve (3) and optional anchoring balloon (50). If the operator chooses to aspirate from distal end hole (4), the bypass catheter (1) can be pulled back so that the side hole (2) is temporarily positioned within sheath (60), which is sized for a snug fit around bypass catheter (1), and aspiration force applied at proximal hole (7) will be transmitted to end hole (4), provided valve (3), when present, is open during said aspiration. It should be noted that for optimal use of this embodiment of the present invention, first segment (5) must fit snugly inside slide-able outer support sheath (60).

It will be understood that the above particular embodiments are shown and described by way of illustration only. The principles and the features of the present disclosure may be employed in various and numerous embodiments thereof without departing from the scope and spirit of the disclosure as claimed. The above-described embodiments illustrate the scope of the disclosure but do not restrict the scope of the disclosure.

What is claimed is:

1. A medical device for ameliorating a blockage in a blood vessel, said medical device comprising:
   (a) a longitudinal structure configured for insertion into said blood vessel, said longitudinal structure defining an inner lumen and including:
      a proximal segment having an open proximal end;
      a distal segment extending from said proximal segment and including an open distal end forming an exit opening aligned with a longitudinal axis of the longitudinal structure; and
      a side hole positioned adjacent to a juncture of said proximal and distal segments, said side hole being in communication with said open distal end to channel blood flow into and through said side hole, around said blockage in said blood vessel, and out said open distal end so as to establish a blood flow bypass around said blockage in said vessel, wherein the longitudinal structure is devoid of exit openings between the side hole and exit opening;
   (b) at least one macerating element supported by said longitudinal structure, the macerating element disposed between the side hole and exit opening and the longitudinal structure is devoid of any balloons between the side hole and exit opening to form an open area;
   (c) an outer sheath slidable in relation to said longitudinal structure to cover said side hole, thereby closing the side hole to stop blood inflow through the side hole and redirect blood flow from the distal end hole to exit through the proximal segment;
   (d) an energy delivery element,
      wherein said energy delivery element is positioned on the distal segment; and
   (e) a single balloon, the single balloon being disposed between the side hole and the proximal opening.

2. The medical device of claim 1, wherein said inner lumen defines a first diameter in said proximal segment a second diameter in said distal segment, said first diameter being less than said second diameter to prevent backflow of blood into said proximal segment.

3. The medical device of claim 1, further including a valve positioned at said juncture of said proximal segment and said distal segment.

4. The medical device of claim 3, wherein said valve is positioned proximally of said side hole and is configured to prevent backflow of blood into said proximal segment.

5. The medical device of claim 1, wherein said longitudinal structure is devoid of any expandable occluding structure distal of the side hole.

6. The medical device of claim 1, wherein said longitudinal structure is configured such that blood flow is directed exclusively out said open distal end when said side hole is exposed from said outer sheath.

7. The medical device of claim 1, further comprising at least one perforation in fluid communication with an outside of the longitudinal structure and in fluid communication with a separate channel.

8. The medical device of claim 1, wherein the at least one perforation is in fluid communication with a separate channel.

9. A medical device for ameliorating a blockage in a blood vessel, said medical device comprising:
   (a) a longitudinal structure defining an inner lumen and having a distal tip defining an open distal end, an open proximal end, at least one perforation in fluid communication with an outside of the longitudinal structure, at least one macerating element adjacent the at least one perforation and distal of a side hole, and the side hole in communication with said open distal end to channel blood flow through said side hole, around said blockage in said blood vessel, and out said open distal end so as to establish a blood flow bypass around said blockage in said vessel;
   (b) an outer sheath slidable in relation to said longitudinal structure to cover said side hole, thereby closing the side hole to stop blood flow in through the side hole and redirect blood flow from the distal end hole through the proximal segment the, the longitudinal structure devoid of balloons between the side hole and open distal end and between the macerating element and open distal end;
   c) an energy delivery element positioned on the distal segment; and d) a single balloon, the single balloon being disposed between the side hole and the proximal opening.

10. The medical device of claim 9, wherein said inner lumen defines a first diameter in said proximal segment and a second diameter in said distal segment, said first diameter being less than said second diameter to prevent backflow of blood into said proximal segment.

11. The medical device of claim 9, further including a valve positioned at a juncture of said proximal segment and said distal segment.

12. The medical device of claim 11, wherein said valve is positioned proximally of said side hole and is configured to prevent backflow of blood into said proximal segment.

13. The medical device of claim 9, wherein said longitudinal structure is configured such that blood flow is directed exclusively out said open distal end when said side hole is exposed from said outer sheath.

14. A method for ameliorating a blockage in a blood vessel using the device of claim 9, said method comprising:
 (a) inserting said open distal end in said blood vessel;
 (b) moving said device longitudinally along said blood vessel until at least one perforation formed in said longitudinal structure is positioned to communicate fluid to said blockage in said blood vessel;
 (c) activating said energy delivery element;
 d) infusing lytics into said blood vessel via said at least one perforation;
 e) repositioning said outer sheath to cover said side hole and thereby facilitate aspiration through said longitudinal structure;
 (f) ceasing said infusion;
 (g) ceasing said aspiration; and
 (h) withdrawing said medical device from said blood vessel.

15. The method of claim 14, further comprising rotating a macerating element to macerate clot.

16. A medical device for ameliorating a blockage in a blood vessel, the medical device comprising:
 a longitudinal structure having proximal and distal openings, the longitudinal structure being configured for insertion into the blood vessel and including:
  a circumferential outer wall with an inner surface circumscribing and defining a central lumen; and
  a side hole formed in the circumferential outer wall and in communication with the central lumen such that blood flow is directed through the side hole, into the central lumen, and out the distal opening, so as to establish a blood flow bypass around the blockage in the vessel;
 an outer sheath slidable in relation to the longitudinal structure to cover the side hole, thereby redirecting blood flow through the distal opening and out the proximal opening in the longitudinal structure;
 a single balloon, the single balloon being disposed between the side hole and the proximal opening, the longitudinal structure devoid of expanding occluding members distal of the side hole; and
 an energy delivery element positioned on a distal region of the longitudinal structure.

17. The medical device of claim 16, wherein the longitudinal structure is configured such that blood flow is directed exclusively between the side hole and the distal opening when the side hole is exposed from the outer sheath.

18. A method for ameliorating a clot in a blood vessel using the device of claim 17, the method comprising
 (a) inserting said open distal end in said blood vessel;
 (b) moving said device longitudinally along said blood vessel until at least one perforation formed in said longitudinal structure is positioned to communicate fluid to said clot in said blood vessel, while said side hole and distal segment provides a bypass channel for blood to flow from proximal to said clot and out said distal opening, thereby providing perfusion to the tissue supplied by the blood vessel (c) activating said energy delivery element;
 (d) infusing lytics into said blood vessel via at least one perforation;
 (e) ceasing said infusion;
 (f) repositioning said outer sheath to cover said side hole and thereby facilitate aspiration through said longitudinal structure when desired;
 (g) rotating a maceration element to macerate said clot;
 (h) ceasing said rotation; and
 (i) applying aspiration.

* * * * *